(12) United States Patent
Butts et al.

(10) Patent No.: US 8,779,770 B2
(45) Date of Patent: Jul. 15, 2014

(54) MOLECULAR STRUCTURE DETERMINATION FROM NMR SPECTROSCOPY

(75) Inventors: Craig P. Butts, Cantock's Close (GB); Jeremy Harvey, Cantock's Close (GB)

(73) Assignee: The University of Bristol, Bristol (GB)

( * ) Notice: Subject to any disclaimer, the term of this patent is extended or adjusted under 35 U.S.C. 154(b) by 545 days.

(21) Appl. No.: 13/061,468

(22) PCT Filed: Sep. 2, 2009

(86) PCT No.: PCT/GB2009/051105
§ 371 (c)(1),
(2), (4) Date: May 19, 2011

(87) PCT Pub. No.: WO2010/026418
PCT Pub. Date: Mar. 11, 2010

(65) Prior Publication Data
US 2011/0210730 A1    Sep. 1, 2011

(30) Foreign Application Priority Data
Sep. 4, 2008   (GB) .................................. 0816100.2

(51) Int. Cl.
*G01V 3/00*    (2006.01)
(52) U.S. Cl.
USPC .......................................... 324/312; 324/310

(58) Field of Classification Search
USPC .................. 324/312, 310, 307, 309
See application file for complete search history.

(56) References Cited

U.S. PATENT DOCUMENTS

| | | | | |
|---|---|---|---|---|
| 4,719,582 A | * | 1/1988 | Ishida et al. | 702/27 |
| 6,150,179 A | * | 11/2000 | Went | 436/173 |
| 7,285,956 B2 | * | 10/2007 | Maeda et al. | 324/318 |

OTHER PUBLICATIONS

Atkinson R A et al., "The direct determination of protein structure by NMR without assignment" FEBS Letters, Elsevier vol. 510, No. 1-2 (2002) pp. 1-4.
Reggelin M et al., "Determination of the relative configuration by distance geometry calculations with proton-proton distances from NOESY spectra" Angew. Chem. Int. Ed. Engl. vol. 33, No. 7 (1994) pp. 753-755.

* cited by examiner

*Primary Examiner* — Louis Arana
(74) *Attorney, Agent, or Firm* — Bret E. Field; Kyle A. Gurley; Bozicevic, Field & Francis LLP

(57) ABSTRACT

Methods for the determination of the molecular structures of compounds are disclosed, the methods comprising obtaining NMR spectroscopic measurements of compounds, determining internuclear distances from the NMR measurements, and inputting the distances to an algorithm to determine probable structures. Optionally, constraints may be added and the algorithm repeated. Usually, the methods do not require comparisons to databases of spectra during the generation of possible structures.

19 Claims, 4 Drawing Sheets

— HSQC correlation

---- H2BC correlation

◡ HMBC correlation

Overall Program Structure:

(Square boxes are subroutines / ovals are modules with arrays etc)

Details for key 'basinhopping' subroutine:

MOLECULAR STRUCTURE DETERMINATION FROM NMR SPECTROSCOPY

FIELD OF THE INVENTION

The present invention relates to methods for the determination of the molecular structure of compounds using NMR (Nuclear Magnetic Resonance) spectroscopic measurements. In particular, the invention entails the use of NMR spectroscopic methods on a molecule in solution, to obtain an array of internuclear distances, and use these in distance-geometry optimisation to determine molecular structure preferably for relatively small organic molecules including the majority of connectivities, and relative stereochemistry where present.

BACKGROUND TO THE INVENTION

Current methods to determine the structure of organic molecules, rely on solid-state structure determination, usually using X-ray crystallography, providing determination of both connectivity and 3-dimensional structure (stereochemistry). In this case a crystal of the material must be available—by no means a given. Also, the structure of the molecule may be affected by the crystalline lattice into which it must conform, hence the determination may be less accurate when compared to solution-based activities.

Alternatively, structure determination may involve mainly spectroscopic techniques, including NMR spectroscopy.

Elyashberg et at (Journal of Analytical Chemistry 63 (1) (2008) p 13-20) discuss an expert system which makes use of a comparison with a large database (400,000 molecular structures and $^{13}C$ and $^{1}H$ NMR spectra) in order to determine molecular structures.

Reggelin et at (Angew. Chem. Int. Ed. Engl. (1994) 33 (7) p 753 to 755) discuss determination of relative configuration by distance geometry calculations from NOESY spectra.

Kock et at (Magn. Reson. Chem. (2004) 42 pp 1042-1045) discuss a method for structure elucidation involving generating all possible structures for a given molecule and comparing the predicted NMR spectra of these structures to the experimentally determined spectra.

Mierke et at (J. Org. Chem. 57 (23) (1992) pp 6365 to 6367) discuss determination of conformation and configuration using NOESY data.

Typically in such a structure determination, a trained chemist or spectroscopist makes a large number of qualitative assessments of spectroscopic properties of the molecule, or its component parts, and combines these with chemical knowledge and spectroscopic experience in order to find an answer which best fits the information available. An often unreliable automated alternative to finding connectivity is for the spectroscopic information to be input to an algorithm which makes the qualitative assessments on the basis of comparison with databases of known compounds and spectra. In these cases, the determination of structure is severely limited by the skill and knowledge of the spectroscopist and the quality of the database and searching algorithms. Compiling databases of structures and spectra is extremely time-consuming and expensive. The method involves comparing spectra with known phenomenon. If a new class of material is studied, this can severely compromise the likelihood or accuracy of structure elucidation. Also, 3-dimensional structure information requires the most detailed analysis of spectra. The spectroscopist must specify a series of experiments usually NOE (Nuclear Overhauser Effect) and/or ROE (Rotational Overhauser Effect) and/or RDC (Residual Dipolar Coupling) targeting 3-D (stereochemical) information, or else undertake a significant analysis of coupling information. Neither of these investigations is by any means guaranteed to work, and depends very strongly upon the nature of the material studied.

There is a need for a method for determining molecular structure which overcomes the problems of the prior art.

SUMMARY OF THE INVENTION

The invention described here aims to provide the determination of both connectivity and 3-dimensional structure in solution, without the need for significant qualitative interpretation of data other than to identify correlations in spectra—which is a relatively trivial task and open to automation, in order to determine molecular structure of a compound.

The present invention accordingly provides a method for the determination of the molecular structure of a compound, the method comprising,
a) obtaining nuclear magnetic resonance spectroscopic measurements of the compound,
b) determining internuclear distances from the nuclear magnetic resonance spectroscopic measurements,
c) inputting the internuclear distances to a distance—geometry algorithm to determine the probable structure(s) of the compound, and
d) optionally, inputting or removing constraints (preferably data constraints) to the algorithm and repeating step (c).

The NMR spectroscopic measurements may include $^{1}H$ NMR spectra, $^{1}H$-$^{1}H$ NOE or ROE measurements, RDC measurements, and $^{1}H$—X, X—X (i.e. homonuclear), or X—Y (i.e. heteronuclear) correlation experiments (where X and Y can be any NMR active nucleus, typically $^{13}C$, $^{15}N$, $^{19}F$, $^{31}P$, $^{11}B$, $^{29}Si$) including HMQC, HSQC, H2BC, HMBC, and INADEQUATE or their numerous variants or direct-detected analogues. The measurements may be 1-dimensional and/or multi-dimensional (2-dimensional, 3-dimensional or of higher dimensions). Preferably the nuclear magnetic resonance spectroscopic measurements are X spectra, X—X and/or X—Y correlation experiments and nuclear Overhauser effect or rotational Overhauser effect measurements, wherein X and Y refer to an active NMR nucleus. Whatever the dimension of the measurement, X and Y may be independently selected from $^{1}H$, $^{13}C$, $^{15}N$, $^{19}F$, $^{31}P$, $^{11}B$, $^{29}Si$, $^{17}O$.

Preferably, the X spectra are 1 dimensional $^{1}H$ spectra, $^{13}C$ spectra and/or $^{15}N$ spectra.

Preferably, the X—X and/or X—Y correlation experiments are selected from 1-bond correlation experiments, 2 bond correlation experiments and/or multiple bond correlation experiments.

Advantageously, the X—X and/or X—Y correlation experiments are selected from one or more of Heteronuclear Single Quantum Coherence (HSQC), HSQC-Total Correlation Spectroscopy (HSQC-TOCSY), Heteronuclear Multiple Bond Correlation (HMBC), Heteronuclear 2 Bond Correlation (H2BC), Incredible Natural Abundance Double Quantum Transfer Experiment (INADEQUATE), Correlated Spectroscopy (COSY), and Total Correlation Spectroscopy (TOCSY) experiments. Other correlation experiments may be conducted depending upon the nature of the compound and available spectrometers.

Preferably, the nuclear Overhauser effect or Overhauser effect measurements are selected from one or more of NOE or ROE, and X—X NOE or ROE measurements, wherein X is preferably $^{1}H$.

Preferably, determining the internuclear distances is from the NOE and/or ROE measurements, preferably the $^1$H NOE and/or $^1$H ROE measurements.

Interproton distances may be assessed by the NOE (or ROE) measurements. Conversion of the measurements into usable distances may be achieved by assuming an $r^{-6}$ relationship between NOE intensity and distance. This allows an array of relative distances to be extracted, based on an internal comparison of each NOE intensity generated by each irradiation. A single, known distance in the molecule allows all of the relative distances to be converted to absolute values. This known distance may, for example, be between diastereotopic methylene units, or vicinal aromatic protons. Comparisons between irradiations may be achieved by standardising against a distance established between the two irradiated nuclei e.g. H1 is irradiated and the distance to H2 (H1–H2) established by comparison with a known distance (e.g. methylene) as above. Then H2 is irradiated and all distances to H2 are calculated by comparison to the H1–H2 distance assessed previously.

Preferably, determining the distances between other pairs of atoms of the compound is from the X—X and/or X—Y correlation experiments, preferably only from the X—X and/or X—Y correlation experiments.

Thus, internuclear distances may be approximated to average standard bond distances based on information from the 1-bond $^1$H—X, X—X or X—Y correlation experiments, and inputting the estimated distances to the distance-geometry algorithm.

Furthermore, the method preferably further comprises a step of estimating typical bond or through-space distances based on connectivity from 2-bond correlation experiments and inputting the estimated distances to the distance-geometry algorithm.

Thus, internuclear distance may also or alternatively be approximated by typical bonding or through-space distances from 2-bond correlation experiments e.g. $H_1$—$X_1$ HSQC correlation and $H_1$—$X_2$ correlation in H2BC implies $X_1$—$X_2$ connectivity and associated bond distance as well as $H_1$—$X_2$ through-space distance, or where sequential connectivities are shown to exist (for example where both $H_1$—$X_1$ and $X_1$—$X_2$ correlations exists, then the $H_1$—$X_2$ distance can be assumed). This includes implicit connectivities in $XH_2$ or $XH_3$ groups.

Also, preferably, the method further comprises a step of determining estimated ranges of bond or special distances based on multiple bond correlation experiments and inputting the estimated ranges to the distance-geometry algorithm.

Thus, internuclear distances may be constrained to a range of values on the basis of multiple bond $^1$H—X or X—X correlation experiments, typically HMBC (heteronuclear multiple bond coherence), where observed correlations are assumed to correspond to a minimum of 1 bond and a maximum of 4 bonds, with the corresponding maximum distance being where intervening bonds are fully extended in an all-trans arrangement.

The distances and distance constraints may then be submitted to the distance-geometry optimisation in order to obtain an array of structures for which a merit function could be evaluated to indicate how closely these structures matched to the input distances. On the basis of the best-fit structure solution, additional data constraints may be added to fulfil chemical demands, including the addition of dummy atoms and/or NMR-inactive nuclei where appropriate. A repeat distance-geometry optimisation may be undertaken and the final step repeated as necessary. Alternative NMR experimental approaches which might also be employed to obtain comparable data constraints for distance-geometry solution include variable temperature experiments, RDC (residual dipolar coupling) experiments, relaxation-based measurements, J-resolved experiments.

Variable temperature experiments are particular useful to resolve conformation (and other information) for a structure.

Alternative data constraints might also be employed in the distance-geometry optimisation, such as angle/torsional constraints arising from coupling constants or implicit hybridisation.

Alternative 'Types' and associated merit functions might be employed to describe these different types of data constraints, such as the angle/torsional data constraints, RDC data constraints, variable temperature NOE data constraints, relaxation-based data constraints.

The method will generally be conducted on a compound (preferably containing at least C and H atoms) dissolved in a suitable solvent. Thus, preferably, the method further comprises the step, before obtaining the NMR spectroscopic measurements, of providing a compound and dissolving the compound in an NMR acceptable solvent to obtain a solution. Usually, the NMR acceptable solvent is a deuterated solvent.

Generally, the method of the invention will be used on compounds of $M_R$<2000 Daltons. Usually, the distance-geometry algorithm will be computer implemented.

A great advantage of the invention is that it does not depend on a database of structures or spectra during the generation of possible structural candidates. Thus, preferably, the method does not comprise a step of comparing the NMR spectroscopic measurements to a computer database of known NMR spectroscopic measurements, nor of known molecular structures during the generation of possible structural candidates. Such databases or steps may or may not be used later in the procedure. If they are used they will generally be used only to confirm the answer (if only 1 possible structure arises) or identify the correct answer from amongst the selection of possible structures generated.

Potential applications of the invention generally involve examining the structure of molecules in-situ in solution. These might include:

(i) determination of the structure of unknown materials generated from chemical synthesis or biological sources;
(ii) determination of stereochemistry in molecules of interest in solution;
(iii) structure determination of active pharmaceuticals in-situ in, for example, protein-ligand complexes;
(iv) determination of conformational/dynamic behaviour in molecules in solution.

DETAILED DESCRIPTION OF THE INVENTION

The invention is further illustrated by the accompanying drawings in which.

Figure 1:
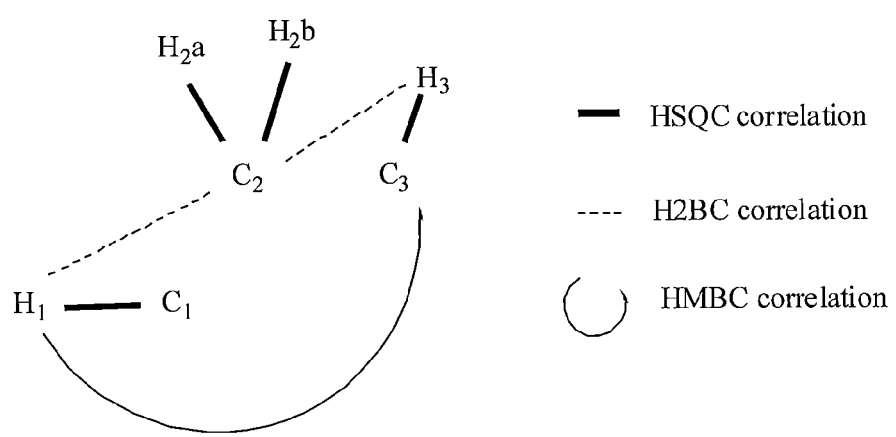
FIG. 1 illustrates example correlations in HSQC, H2BC and HMBC NMR measurements.

This invention has been applied in a case study of Strychnine, where $^1$H, NOE, HSQC, H2BC, HMBC, INEPT-INADEQUATE and $^{15}$N-HMBC measurements and analysis, gave rise to 46 interproton distances, 22 $^1$H-$^{13}$C 1-bond distances, 36 $^1$H-$^{13}$C 2-bond distances, 8 $^{13}$C-$^{13}$C 2-bond distances, 20 $^{13}$C-$^{13}$C 1-bond distances and 38 2 or 3-bond constraints including C—N constraints.

In the case of Strychnine, all of the C—C, C—H connectivities were established, as were the relative stereochemistries at stereogenic centres. Absolute stereochemistry was not established.

For more complete structure determination, the aromatic carbons and hydrogens (identified by chemical shift and correlation spectra) were then constrained to typical aromatic distances, and addition of N and O atoms was achieved as follows:

On the basis of the initial model structure, an oxygen was added and constrained to a typical carbonyl bond distance from a non-protonated carbon with a chemical shift seen by HMBC to be clearly in the carbonyl region. Then the two nitrogen atoms and ether oxygen were added as dummy atoms and constrained to typical C—X bonding distances to the nearest carbon atoms with empty valence. Further distance-geometry optimisation allows the full structure to be determined with all heavy atoms in place. Again, the initial model structures which most closely fit the input distances can be considered to be the best match to the molecular structure in solution for Strychnine.

The method of the invention will now, by way of example, be described in more detail.

Method

Acquisition and Processing of NMR Spectra

Obtained at 500 MHz using a Varian VNMRS500 spectrometer equipped with a broadband autotune or indirect observe ($^1$H, $^{13}$C, $^{15}$N) probe. Samples were typically prepared in 5-100 mg/ml concentrations in a deuterated solvent, normally CDCl$_3$:

$^1$H NMR spectrum—4 s acquisition time, 2 s relaxation delay, sweep width 20 ppm, Hz, 45° flip angle, 16 scans. Data processing: lb=1, zero-filled to 128 k data points.

$^{13}$C NMR spectrum—2 s acquisition time, 2 s relaxation delay, sw=300 ppm, 45° flip angle, 400 scans. Data processing: lb=3, zero-filled to 128 k data points.

Gradient-HSQC spectrum—2 scans per 2×128 t1 increments, 1500 t2 points, sweep widths (F1 200 ppm, F2 10 ppm). Data processing: Window functions applied (t1 GM=100, t2 GM=14.29) linear prediction in t1 to 512 points, zero-filled to 2 k×2 k data points prior to fourier transform.

Gradient-H2BC spectrum—2 scans per 2×190 t1 increments, 1500 t2 points, sweep widths (F1 200 ppm, F2 10 ppm). Data processing: linear prediction in t1 to 512 points, zero-filled to 2 k×2 k data points prior to fourier transform.

Gradient-HMBC spectrum—2 scans per 2×256 t1 increments, 1500 t2 points, sweep widths (F1 300 ppm, F2 10 ppm). Data processing: Window functions applied (t1 GM=100, t2 shifted Sq. sine=13.33+0.075) linear predicted to 512 data points, zero-filled to 2 k×2 k data points prior to fourier transform.

1D-DPFGSE NOE spectra—64 to 2048 scans per irradiation, 4 s acquisition time, 2 s relaxation delay, sweep width 10 ppm, Hz, 45° flip angle. Data processing: lb=5, zero-filled to 128 k data points.

Analysis of NMR Spectra and Extraction of Approximate Distance Information

Spectra processed as above were analysed as follows:

Labelling of $^1$H and $^{13}$C Peaks:

Correlations in the HSQC allowed the labelling of protons ($^1$H) and carbons ($^{13}$C) through their chemical shifts i.e.
a (1H, 13C) correlation centred at (4.3 ppm, 67 ppm) identifies a proton resonance centred at 4.3 ppm and a $^{13}$C resonance centred at 67 ppm.

Correlations in the HMBC spectrum which showed $^1$H or $^{13}$C signals that did not correspond to those previously identified in the HSQC allow labelling of protons not attached to carbon (NH, OH, SH etc) and unprotonated carbons.

Distances from correlation spectra (observed correlations schematically illustrated in FIG. 1) are now determined and assigned to either type 1 (rigid distance constraint) or type 2 (distance range) as described below:

Correlations in the HSQC (say between H1 and C1) are assigned a corresponding distance between H1 and C1—approximately 1.1 Å (type 1).

Correlations in the H2BC (say between H1 and C2) give rise to a distance between H1 and C2—approximately 2.2 Angstroms (type 1).

The H2BC correlation between H1 and C2 also implies a similar relationship for protons on C2 (say H2a and H2b) and C1 hence giving rise to distances between H2a-C1 and H2b-C1—approximately 2.2 Angstroms (type 1).

The combination of H1-C1 HSQC and H1-C2 H2BC correlations gives rise to a distance between C1 and C2—approximately 1.5 Angstroms (type 1).

H2BC correlations from two protons to the same carbon (say H1 to C2 and H3 to C2), along with their HSQC correlation (H1-C1 and H3-C3) gives rise to a C1-C3 distance—approximately 2.5 Angstroms (type 1).

The HMBC correlation between H1 and C3 combined with the H1-C1 HSQC correlation, imposes a constrained range of possible distances between C1 and C3—distance range is initially set to be between approximately 1.5-3 Angstroms (type 2).

Distances from NOE Spectra:

Integrals (peak areas above baseline) are obtained for all of the positive NOE signals (relative to the large negative selective inversion peak). Peaks with significant negative intensity (antiphase character, lineshape distortion or inverted intensity) are considered artifacts and ignored in the first instance.

Conversion of NOE integrals into distances is achieved by assuming a relationship between a protons NOE intensity (integral), say H2b or H1, and the corresponding distance of that proton to the selectively irradiated proton, say H2a. A relationship of $r^{-6}$ is assumed (where r is the H—H distance). Hence upon irradiating H2a in a 1D-NOESY experiment, the ratio of the NOE integrals for H2b and H1 corresponds to the ratio of their $r^{-6}$ adjusted distances to H1.

i.e.

$$\text{On irradiation of } H2a \text{ in 1D-NOESY experiment} \frac{\text{Distance }(H1-H2a)}{\text{Distance }(H2b-H2a)} = \left(\frac{\text{Integral }(H2b\ NOE)}{\text{Integral }(H1\ NOE)}\right)^{1/6}$$

Equation 1—exemplar calculation of internuclear distance relationships with NOE integrals Thus all of the relative distances to the irradiated proton can be extracted for resonances observed in a given NOE spectrum by using Equation 1.

Figure 3:
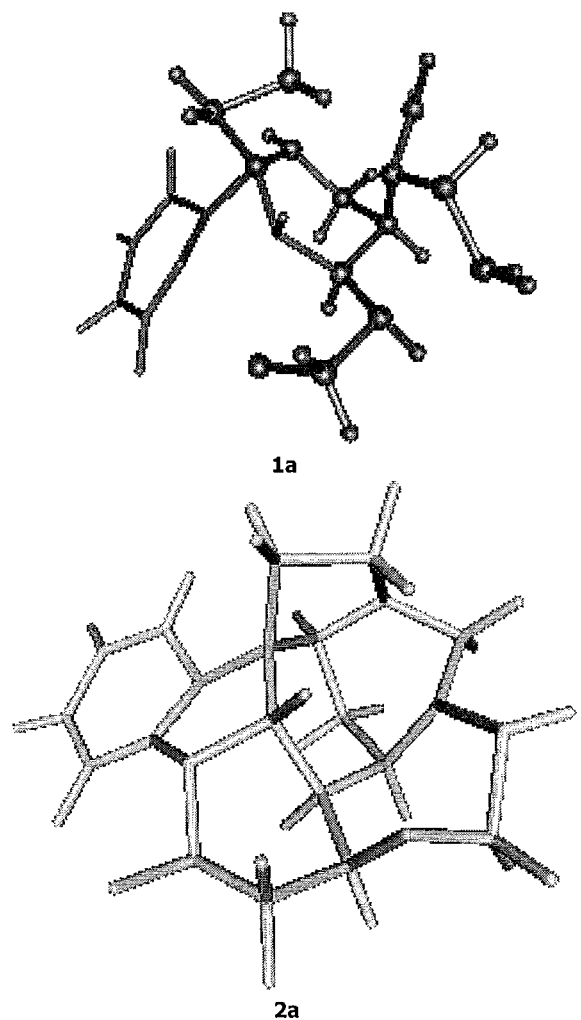
FIG. 3 illustrates structures of strychnine geometries solved for $^1$H and $^{13}$C skeleton only (1a) and following addition of nitrogens and oxygens (2a)

A single assumed 'calibration' distance in one NOE spectrum allows all of the relative distances to be converted to absolute distances—this 'calibration' distance is usually between diastereotopic methylene protons ($CH_2$), or vicinal aromatic protons. For the example in FIG. 3, H2a and H2b show a correlation to the same carbon in the HSQC, and are thus assigned an approximate H2a-H2b distance of 1.78 Å. Applying Equation 1 to this H2a-H2b distance and using the integrals of the NOE spectrum, a value for the H2a-H1 distance (and any other measurable distances to H2a) can be obtained.

Comparisons between NOE spectra are then achieved by standardising against a distance already established e.g. In the NOESY spectrum for H1, the distance to H2a (H2a-H1) has already established above, hence the H2a-H1 distance is then used as the 'calibration' distance for the H1 NOESY spectrum then measurable interproton distances to H1 can be determined.

This process is repeated until all NOESY spectra have been analysed. Some NOESY spectra may not contain a resonance for which a 'calibration distance has been determined—in this case it may be necessary to use more than one intermethylene or aromatic distance as calibration distances.

Where a distance is determined twice from NOEs, e.g. H3-H4 might be determined by a NOESY experiment on H3 and by a NOESY experiment on H4, the average value of the two determined distances is taken for the value of if the distance.

Distance-Geometry Solution

Prior to Distance-Geometry solution, any duplicate distances are removed—where appropriate type 2 distance ranges are removed if the corresponding Type 1 distances are already determined.

All of the distances determined above are submitted to a distance-geometry algorithm to generate 3-dimensional structures by global optimisation of a figure of merit function relating structure to the goodness of fit between distances in the structure and the input distance matrix.

The merit function was based on a sum of three types of distance constraint terms, Type 1 for the 1- and 2-bond correlation distances (from HSQC/H2BC data), Type 2 for HMBC distance ranges, and Type 3 for NOE distances respectively. A repulsive term between all pairs of atoms for which no distance was defined was also included to prevent accidental overlap of these unrestrained atom pairs. Global optimization was performed using a modified Monte Carlo minimization process.

Figure 2:
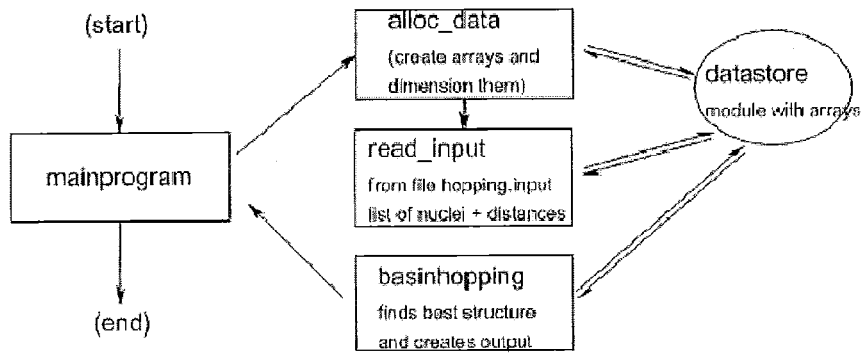
FIG. 2 is a plan of a distance-geometry algorithm useful in implementing the present invention.
Figure 2:
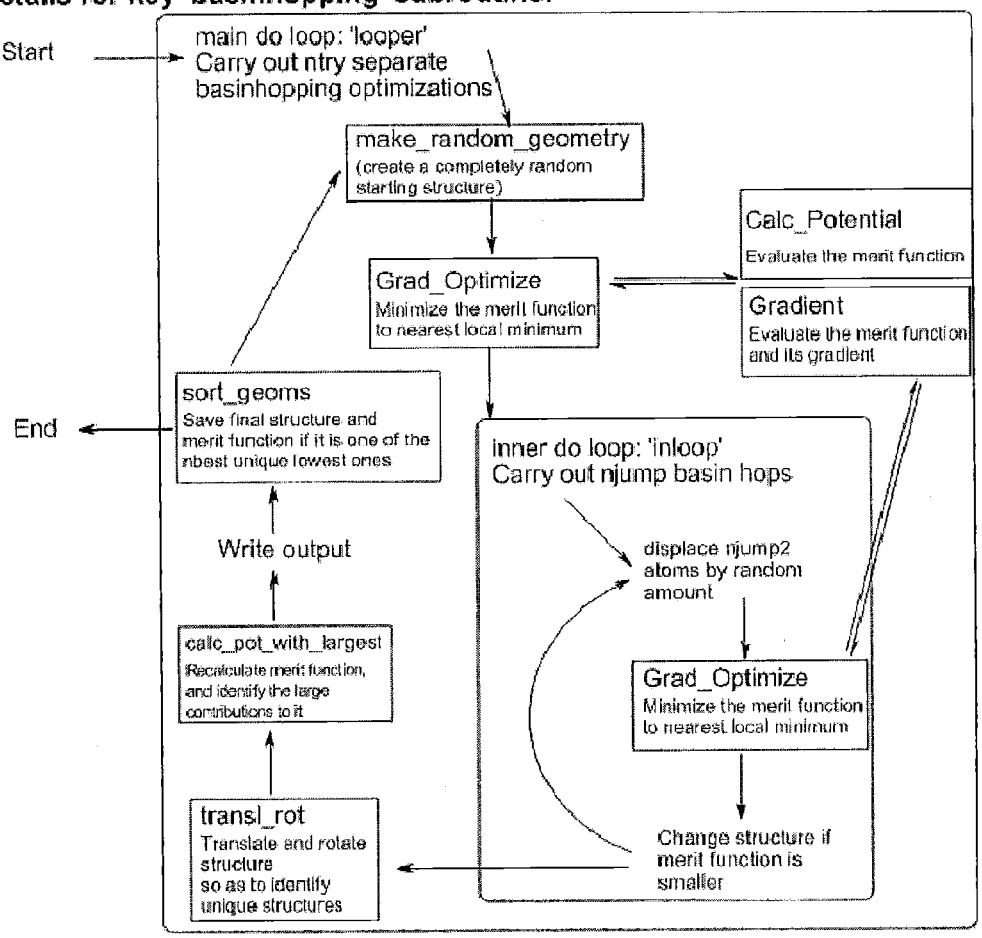

The distance-geometry algorithm is described in FIG. 2.

Distance-Geometry Refinement

Where preliminary distance-geometry gives a reasonable solution (or set of solutions), subsequent distance-geometry procedures are conducted on modified input distance lists arising from the following steps (order is not crucial):

(i) Distance constraints for H—C and C—C distances are modified to account for the hybridisation at carbon centres—$sp^3$ hybridisation being inherent in any carbon centres bound to 4 different carbons/protons, and $sp^2$ hybridisation being identified by a combination of valency—a double bond requiring two adjacent trivalent carbons—and the carbon chemical shift ($\delta > \sim 100$ ppm) for each remaining centre. Geometry-based identification of hybridisation is not feasible at this stage in the refinement given the relative inaccuracy in nuclear positions.

(ii) Known chemical features can be constrained to physically reasonable geometries—for example an aromatic ring, which is readily identified from the correlation spectra and a chemical shift assessment, can be constrained to planarity by the application of distance constraints between pairs of ortho-, meta- and para-protons (~2.8 Å, ~4.3 Å and ~5 Å respectively) within the benzene ring.

(iii) Distances/connectivity of other nuclei can be introduced. NMR active nuclei (such as nitrogen) can be incorporated in a comparable fashion to $^{13}C$ through the corresponding HMBC experiment (such as $^1H$-$^{15}N$ HMBC), or (along with non-NMR active nuclei) through a fulfillment of missing valencies and carbon chemical shifts. For example, carbonyl oxygen position could be identified on the basis of a carbon having a very high chemical shift (~150-220 ppm) and missing valency (two or more bonds).

(iv) Type 2 distance ranges (especially to quaternary centres) can be modified to recognise the bonding which is apparent in the structure solution—for example, those which are now clearly 2-bond in nature can be changed to appropriate Type 1 values—~1.5 Angstroms in this case.

(v) Distances can be added based on additional spectroscopic information available, for example, $^1H$-$^1H$ coupling constants measured from the NMR spectra can be used to constrain interproton distances where other data have been inconclusive.

Iterative solutions may be used to obtain a final refined structure by repeating the steps above and employing chemical knowledge to impose distances where these are chemically or physically reasonable.

The invention is further illustrated by the following examples.

EXAMPLE 1

Strychnine

~50 mg of Strychnine was dissolved in 0.6 ml of $CDCl_3$ and transferred to a 5 mm NMR tube (Norell 500-7). NMR experiments (see below) were conducted a Varian VNMRS500 spectrometer equipped with a tuneable direct observe (X/H) probe, using the VNMRJ2.2C software and ChemPack 4.1 (2008 Feb. 15) interface and experiments. Data was transformed, phased and baseline corrected before integration using ACDLabs software. Experiments performed were:

$^1H$ NMR spectrum—~4 s acquisition time, 2 s relaxation delay, sweep width 20 ppm, Hz, 45° flip angle, 16 scans. Data processing: lb=1, zero-filled to 128 k data points.

$^{13}C$ NMR spectrum—2 s acquisition time, 2 s relaxation delay, sw=300 ppm, 45° flip angle, 400 scans. Data processing: lb=3, zero-filled to 128 k data points.

Gradient-HSQC spectrum—2 scans per 2×128 t1 increments, 1500 t2 points, sweep widths (F1 200 ppm, F2 10 ppm). Data processing: Window functions applied (t1 GM=100, t2 GM=14.29) linear prediction in t1 to 512 points, zero-filled to 2 k×2 k data points prior to fourier transform.

Gradient-H2BC spectrum—2 scans per 2×190 t1 increments, 1500 t2 points, sweep widths (F1 200 ppm, F2 10 ppm). Data processing: linear prediction in t1 to 512 points, zero-filled to 2 k×2 k data points prior to fourier transform.

Gradient-HMBC ($^{13}C$) spectrum—2 scans per 2×256 t1 increments, 1500 t2 points, sweep widths (F1 300 ppm, F2 10 ppm). Data processing: Window functions applied (t1 GM=100, t2 shifted Sq. sine=13.33+0.075) linear predicted to 512 data points, zero-filled to 2 k×2 k data points prior to fourier transform.

Gradient-HMBC ($^{15}$N) spectrum—2 scans per 2×64 t1 increments, 1500 t2 points, sweep widths (F1 300 ppm, F2 10 ppm). Data processing: Window functions applied (t1 GM=400, t2 shifted Sq. sine=13.33+0.075) linear predicted to 128 data points, zero-filled to 2 k×2 k data points prior to fourier transform.

1D-DPFGSE NOE spectra—64 to 2048 scans per irradiation, 4 s acquisition time, 2 s relaxation delay, sweep width 10 ppm, Hz, 45° flip angle. Data processing: lb=5, zero-filled to 128 k data points.

Distance-Geometry Solution was conducted on initial distances obtained directly from analysis of NMR spectra:

Results from HSQC spectra gave rise to 6 H—H Type 1 distances of 1.76 Angstroms (Entries 1-6 in Table 1, below)

Results from HSQC spectra gave rise to 22 H—C Type 1 distances of ~1.1 Angstroms (Entries 47-68 in Table 1, below)

Results from H2BC spectra gave rise to 27 H—C Type 1 distances of ~2.2 Angstroms (Entries 69-95 in Table 1, below)

Combination of HSQC and H2BC spectra gave rise to 11 Type 1 C—C distances of ~1.5 Angstroms ((Entries 127-137 in Table 1, below)

Combination of HSQC and H2BC spectra gave rise to 8 Type 1 C—C distances of ~2.5 Angstroms ((Entries 96-103 in Table 1, below)

Results from HMBC spectra gave rise to 33 C—C Type 2 distance ranges (Entries 104-126 and 141-151 in Table 1, NB: Entries 141-151 were modified in the refinement steps to be Type 1 distances—see below).

Analysis of NOE spectra gave rise to 40 further H—H Type 3 distances (Entries 7-46 in Table 1, below)

Merit functions employed were:

Type 1: $C1*(1-r/rref)^2$

Type 2: $C2*(1-r/rref)^2$ if r>rref or if r<1.5, 0 otherwise

Type 3: $C3*(1-r/rref)^2$

Repulsive term: $C4*\exp(-r*C5)$

Where C1=1, C2=1, C3=0.2, C4=500, C5=8

Following the initial structure solution, some distances were modified and additional distances were introduced to:

Type 2 constraints for quaternary carbons were shorted

Account for now apparent connectivity and/or hybridisation: C—C distances of 1.5 Angstroms were modified to 1.4 Angstroms or 1.54 Angstroms to recognise single/double-bond nature (Entries 127-137 in Table 1, below); HMBC Type 2 constraints modified to Type 1 where C—C bonds were identified (Entries 141-151 in Table 1, below).

Constrain the aromatic ring to planarity (Entries 138-140, 152-157, 171-174 added)

Addition of Nitrogen and Oxygen atoms through $^{15}$N HMBC (using same approach as outlined for $^{13}$C) and fulfilment of valency/chemical shift (Entries 158-170 in Table 1, below—NB nitrogen entries 158-160 and 168-170 were subsequently converted to Type 1 when the connectivity became apparent during the refinement process.

TABLE 1

Full 174 distance matrix employed for Strychnine (atom labelling can be arbitrary, but in this case is based on the accepted numbering for strychnine.)

| Entry | Atom 1 | Atom 2 | Distance (Å) | Distance Type[a] |
|---|---|---|---|---|
| 1 | H15a | H15b | 1.76 | 1 |
| 2 | H11b | H11a | 1.76 | 1 |
| 3 | H20a | H20b | 1.76 | 1 |
| 4 | H18b | H18a | 1.76 | 1 |
| 5 | H17a | H17b | 1.76 | 1 |
| 6 | H23a | H23b | 1.76 | 1 |
| 7 | H15a | H13 | 2.18 | 3 |
| 8 | H15a | H14 | 2.5 | 3 |
| 9 | H15a | H16 | 2.42 | 3 |
| 10 | H15a | H8 | 4.29 | 3 |
| 11 | H15a | H1 | 3.78 | 3 |
| 12 | H15b | H14 | 2.43 | 3 |
| 13 | H15b | H20b | 2.17 | 3 |
| 14 | H15b | H16 | 2.43 | 3 |
| 15 | H15b | H8 | 4.43 | 3 |
| 16 | H8 | H11b | 2.65 | 3 |
| 17 | H8 | H18b | 2.2 | 3 |
| 18 | H8 | H22 | 3.75 | 3 |
| 19 | H8 | H13 | 2.96 | 3 |
| 20 | H8 | H12 | 3.65 | 3 |
| 21 | H8 | H23b | 4.26 | 3 |
| 22 | H8 | H23a | 4.5 | 3 |
| 23 | H8 | H16 | 4.5 | 3 |
| 24 | H13 | H12 | 2.2 | 3 |
| 25 | H13 | H11b | 3.79 | 3 |
| 26 | H13 | H14 | 2.21 | 3 |
| 27 | H13 | H4 | 3.96 | 3 |
| 28 | H12 | H11b | 3.21 | 3 |
| 29 | H12 | H23a | 2.22 | 3 |
| 30 | H12 | H23b | 2.88 | 3 |
| 31 | H12 | H11a | 2.19 | 3 |
| 32 | H12 | H14 | 2.74 | 3 |
| 33 | H16 | H20b | 3.33 | 3 |
| 34 | H16 | H1 | 2.17 | 3 |
| 35 | H16 | H18a | 3.65 | 3 |
| 36 | H16 | H18b | 4.01 | 3 |
| 37 | H11b | H23b | 3.87 | 3 |
| 38 | H11b | H23a | 4.49 | 3 |
| 39 | H20a | H18b | 2.43 | 3 |
| 40 | H20a | H22 | 2.27 | 3 |
| 41 | H20a | H16 | 4.27 | 3 |
| 42 | H18b | H22 | 2.91 | 3 |
| 43 | H20b | H14 | 3.29 | 3 |
| 44 | H22 | H23a | 2.38 | 3 |
| 45 | H22 | H23b | 2.7 | 3 |
| 46 | H22 | H14 | 3.69 | 3 |
| 47 | H1 | C1 | 1.09 | 1 |
| 48 | H2 | C2 | 1.09 | 1 |
| 49 | H3 | C3 | 1.09 | 1 |
| 50 | H4 | C4 | 1.09 | 1 |
| 51 | H8 | C8 | 1.09 | 1 |
| 52 | H11a | C11 | 1.09 | 1 |
| 53 | H11b | C11 | 1.09 | 1 |
| 54 | H12 | C12 | 1.09 | 1 |
| 55 | H13 | C13 | 1.09 | 1 |
| 56 | H14 | C14 | 1.09 | 1 |
| 57 | H15a | C15 | 1.09 | 1 |
| 58 | H15b | C15 | 1.09 | 1 |
| 59 | H16 | C16 | 1.09 | 1 |
| 60 | H17a | C17 | 1.09 | 1 |
| 61 | H17b | C17 | 1.09 | 1 |
| 62 | H18a | C18 | 1.09 | 1 |
| 63 | H18b | C18 | 1.09 | 1 |
| 64 | H20a | C20 | 1.09 | 1 |
| 65 | H20b | C20 | 1.09 | 1 |
| 66 | H22 | C22 | 1.09 | 1 |
| 67 | H23a | C23 | 1.09 | 1 |
| 68 | H23b | C23 | 1.09 | 1 |
| 69 | H1 | C2 | 2.17 | 1 |
| 70 | H2 | C1 | 2.17 | 1 |
| 71 | H2 | C3 | 2.17 | 1 |
| 72 | H3 | C2 | 2.17 | 1 |
| 73 | H3 | C4 | 2.17 | 1 |
| 74 | H4 | C3 | 2.17 | 1 |

TABLE 1-continued

Full 174 distance matrix employed for Strychnine (atom labelling can be arbitrary, but in this case is based on the accepted numbering for strychnine.)

| Entry | Atom 1 | Atom 2 | Distance (Å) | Distance Type[a] |
|---|---|---|---|---|
| 75 | H8 | C13 | 2.17 | 1 |
| 76 | H11a | C12 | 2.17 | 1 |
| 77 | H11b | C12 | 2.17 | 1 |
| 78 | H12 | C11 | 2.17 | 1 |
| 79 | H12 | C13 | 2.17 | 1 |
| 80 | H13 | C12 | 2.17 | 1 |
| 81 | H13 | C8 | 2.17 | 1 |
| 82 | H13 | C14 | 2.17 | 1 |
| 83 | H14 | C15 | 2.17 | 1 |
| 84 | H15a | C14 | 2.17 | 1 |
| 85 | H15a | C16 | 2.17 | 1 |
| 86 | H15b | C14 | 2.17 | 1 |
| 87 | H15b | C16 | 2.17 | 1 |
| 88 | H16 | C15 | 2.17 | 1 |
| 89 | H17a | C18 | 2.17 | 1 |
| 90 | H17b | C18 | 2.17 | 1 |
| 91 | H18a | C17 | 2.17 | 1 |
| 92 | H18b | C17 | 2.17 | 1 |
| 93 | H22 | C23 | 2.17 | 1 |
| 94 | H23a | C22 | 2.17 | 1 |
| 95 | H23b | C22 | 2.17 | 1 |
| 96 | C1 | C3 | 2.53 | 1 |
| 97 | C2 | C4 | 2.53 | 1 |
| 98 | C11 | C13 | 2.53 | 1 |
| 99 | C12 | C8 | 2.53 | 1 |
| 100 | C8 | C14 | 2.53 | 1 |
| 101 | C12 | C14 | 2.53 | 1 |
| 102 | C13 | C15 | 2.53 | 1 |
| 103 | C14 | C16 | 2.53 | 1 |
| 104 | C8 | C18 | 3.8 | 2 |
| 105 | C8 | C6 | 3.8 | 2 |
| 106 | C8 | C5 | 3.8 | 2 |
| 107 | C11 | C5 | 3.8 | 2 |
| 108 | C12 | C7q | 3.8 | 2 |
| 109 | C12 | C=O | 3.8 | 2 |
| 110 | C13 | C21q | 3.8 | 2 |
| 111 | C15 | C12 | 3.8 | 2 |
| 112 | C15 | C7q | 3.8 | 2 |
| 113 | C15 | C18 | 3.8 | 2 |
| 114 | C15 | C21q | 3.8 | 2 |
| 115 | C16 | C20 | 3.8 | 2 |
| 116 | C16 | C6 | 3.8 | 2 |
| 117 | C17 | C16 | 3.8 | 2 |
| 118 | C17 | C6 | 3.8 | 2 |
| 119 | C18 | C7q | 3.8 | 2 |
| 120 | C20 | C14 | 3.8 | 2 |
| 121 | C20 | C15 | 3.8 | 2 |
| 122 | C22 | C14 | 3.8 | 2 |
| 123 | C22 | C20 | 3.8 | 2 |
| 124 | C23 | C12 | 3.8 | 2 |
| 125 | C23 | C13 | 3.8 | 2 |
| 126 | C23 | C21q | 3.8 | 2 |
| 127 | C1 | C2 | 1.4 | 1 |
| 128 | C2 | C3 | 1.4 | 1 |
| 129 | C3 | C4 | 1.4 | 1 |
| 130 | C8 | C13 | 1.54 | 1 |
| 131 | C13 | C14 | 1.54 | 1 |
| 132 | C13 | C12 | 1.54 | 1 |
| 133 | C12 | C11 | 1.54 | 1 |
| 134 | C14 | C15 | 1.54 | 1 |
| 135 | C15 | C16 | 1.54 | 1 |
| 136 | C17 | C18 | 1.54 | 1 |
| 137 | C22 | C23 | 1.54 | 1 |
| 138 | H1 | H2 | 2.5 | 1 |
| 139 | H2 | H3 | 2.5 | 1 |
| 140 | H3 | H4 | 2.5 | 1 |
| 141 | C4 | C5 | 1.4 | 1 |
| 142 | C5 | C6 | 1.4 | 1 |
| 143 | C6 | C1 | 1.4 | 1 |
| 144 | C6 | C7q | 1.54 | 1 |
| 145 | C7q | C8 | 1.54 | 1 |
| 146 | C20 | C21q | 1.54 | 1 |
| 147 | C21q | C22 | 1.54 | 1 |
| 148 | C14 | C21q | 1.54 | 1 |
| 149 | C7q | C17 | 1.54 | 1 |
| 150 | C11 | C=O | 1.54 | 1 |
| 151 | C16 | C7q | 1.54 | 1 |
| 152 | C1 | C4 | 2.78 | 1 |
| 153 | C2 | C5 | 2.78 | 1 |
| 154 | C3 | C6 | 2.78 | 1 |
| 155 | H1 | H3 | 4.3 | 1 |
| 156 | H2 | H4 | 4.3 | 1 |
| 157 | H1 | H4 | 4.99 | 1 |
| 158 | NCO | C8 | 1.45 | 1 |
| 159 | NCO | C=O | 1.45 | 1 |
| 160 | NCO | C5 | 1.45 | 1 |
| 161 | O=C | C=O | 1.32 | 1 |
| 162 | O=C | C11 | 2.2 | 1 |
| 163 | O=C | NCO | 2.2 | 1 |
| 164 | O2 | C12 | 1.45 | 1 |
| 165 | O2 | C23 | 1.45 | 1 |
| 166 | O2 | C22 | 2.4 | 1 |
| 167 | O2 | C13 | 2.4 | 1 |
| 168 | N2 | C16 | 1.45 | 1 |
| 169 | N2 | C18 | 1.45 | 1 |
| 170 | N2 | C20 | 1.45 | 1 |
| 171 | C5 | C7q | 2.5 | 1 |
| 172 | C1 | C7q | 2.5 | 1 |
| 173 | C6 | NCO | 2.45 | 1 |
| 174 | C4 | NCO | 2.45 | 1 |

[a]Type 1 = rigid distance (HSQC, H2BC or aromatic constraint), Type 2 = HMBC distance range ('Distance' entry refers to upper bound), Type 3 = NOE distance.

Result

The solution-state structure (2a in FIG. 3) elucidated is comparable in constitution, configuration and conformation to solid-state structures obtained from X-ray crystallography. There are some deviations in the local geometry of the atoms, but these do not detract from the qualitatively correct solution obtained

EXAMPLE 2

Synthetic Intermediate in stemona Alkaloid Synthesis

~20 mg of the Stemona alkaloid synthetic intermediate was dissolved in 0.6 ml of $CDCl_3$ and transferred to a 5 mm NMR tube (Norell 500-7). NMR experiments (see below) were conducted using a Varian VNMRS500 spectrometer equipped with a tuneable direct observe (X/H) probe or triple resonance (H/C/X) probe, using the VNMRJ2.2C software and ChemPack 4.1 (2008 Feb. 15) interface and experiments. Data was transformed, phased and baseline corrected before integration using ACDLabs software. Experiments performed were:

$^1$H NMR spectrum—4 s acquisition time, 2 s relaxation delay, sweep width 20 ppm, Hz, 45° flip angle, 16 scans. Data processing: lb=1, zero-filled to 128 k data points.

$^{13}$C NMR spectrum—2 s acquisition time, 2 s relaxation delay, sw=300 ppm, 45° flip angle, 400 scans. Data processing: lb=3, zero-filled to 128 k data points.

Gradient-HSQC spectrum—2 scans per 2×128 t1 increments, 1500 t2 points, sweep widths (F1 200 ppm, F2 10 ppm). Data processing: Window functions applied (t1 GM=100, t2 GM=14.29) linear prediction in t1 to 512 points, zero-filled to 2 k×2 k data points prior to fourier transform.

Gradient-H2BC spectrum—2 scans per 2×190 t1 increments, 1500 t2 points, sweep widths (F1 200 ppm, F2 10 ppm). Data processing: linear prediction in t1 to 512 points, zero-filled to 2 k×2 k data points prior to fourier transform.

Gradient-HMBC spectrum—2 scans per 2×256 t1 increments, 1500 t2 points, sweep widths (F1 300 ppm, F2 10 ppm). Data processing: Window functions applied (t1 GM=100, t2 shifted Sq. sine=13.33+0.075) linear predicted to 512 data points, zero-filled to 2 k×2 k data points prior to fourier transform.

1D-DPFGSE NOE spectra—64 to 2048 scans per irradiation, 4 s acquisition time, 2 s relaxation delay, sweep width 10 ppm, Hz, 45° flip angle. Data processing: lb=5, zero-filled to 128 k data points.

Distance-Geometry Solution was conducted on initial distances obtained directly from analysis of NMR spectra:

Results from HSQC spectra gave rise to 6 H—H Type 1 distances of 1.76 Angstroms (Entries 70-78 in Table 1, below)

Results from HSQC spectra gave rise to 21H—C Type 1 distances of ~1.1 Angstroms (Entries 1-21 in Table 1, below)

Results from H2BC spectra gave rise to 32 H—C Type 1 distances of ~2.2 Angstroms (Entries 32-60 and 80-82 in Table 1, below)

Combination of HSQC and H2BC spectra gave rise to 11 Type 1 C—C distances of ~1.5 Angstroms ((Entries 22-31 and 79 in Table 1, below)

Combination of HSQC and H2BC spectra gave rise to 8 Type 1 C—C distances of ~2.5 Angstroms ((Entries 61-69 in Table 1, below)

Results from HMBC spectra gave rise to 33 C—C Type 2 distance ranges (Entries 83-94, 101, 107-109 and 111 in Table 1, NB: Most of these entries were subsequently modified in the refinement steps to be Type 1 distances—see below).

Analysis of NOE spectra gave rise to 34 further H—H Type 3 distances (Entries 112-145 in Table 1, below)

Merit functions employed were:

Type 1: $C1*(1-r/rref)^2$

Type 2: $C2*(1-r/rref)^2$ if r>rref or if r<1.5, 0 otherwise

Type 3: $C3*(1-r/rref)^2$

Repulsive term: $C4*exp(-r*C5)$

Where C1=1, C2=1, C3=0.2, C4=500, C5=8

Following the initial structure solution, some distances were modified and additional distances were introduced to:

Type 2 constraints for quaternary carbons were shortened to allow easier identification of connectivities.

HMBC Type 2 constraints modified to Type 1 as C—C bonds were identified (Entries 79-88, in Table 1, below).

Addition of Oxygen atoms through fulfillment of valency/chemical shift (Entries 95-100, 102-106 and 110 in Table 1, below).

TABLE 2

Full 145 distance matrix employed for stemona alkaloid synthetic intermediate (atom labelling in this case is arbitrary)

| | Atom 1 | Atom 2 | Distance (Å) | Distance Type[a] |
|---|---|---|---|---|
| 1 | H1a | C1 | 1.09 | 1 |
| 2 | H1b | C1 | 1.09 | 1 |
| 3 | H1c | C1 | 1.09 | 1 |
| 4 | H3a | C3 | 1.09 | 1 |
| 5 | H3b | C3 | 1.09 | 1 |
| 6 | H5a | C5 | 1.09 | 1 |
| 7 | H5b | C5 | 1.09 | 1 |
| 8 | H7 | C7 | 1.09 | 1 |
| 9 | H8a | C8 | 1.09 | 1 |
| 10 | H8b | C8 | 1.09 | 1 |
| 11 | H9a | C9 | 1.09 | 1 |
| 12 | H9b | C9 | 1.09 | 1 |
| 13 | H10a | C10 | 1.09 | 1 |
| 14 | H10b | C10 | 1.09 | 1 |
| 15 | H11 | C11 | 1.09 | 1 |
| 16 | H12 | C12 | 1.09 | 1 |
| 17 | H13 | C13 | 1.09 | 1 |
| 18 | H16a | C16 | 1.09 | 1 |
| 19 | H16b | C16 | 1.09 | 1 |
| 20 | H18 | C18 | 1.09 | 1 |
| 21 | H19 | C19 | 1.09 | 1 |
| 22 | C1 | C3 | 1.54 | 1 |
| 23 | C3 | C7 | 1.54 | 1 |
| 24 | C5 | C16 | 1.54 | 1 |
| 25 | C5 | C11 | 1.54 | 1 |
| 26 | C13 | C19 | 1.54 | 1 |
| 27 | C7 | C19 | 1.54 | 1 |
| 28 | C7 | C12 | 1.54 | 1 |
| 29 | C9 | C10 | 1.54 | 1 |
| 30 | C11 | C18 | 1.54 | 1 |
| 31 | C12 | C18 | 1.54 | 1 |
| 32 | H1a | C3 | 2.17 | 1 |
| 33 | H1b | C3 | 2.17 | 1 |
| 34 | H1c | C3 | 2.17 | 1 |
| 35 | H3a | C1 | 2.17 | 1 |
| 36 | H3b | C1 | 2.17 | 1 |
| 37 | H3a | C7 | 2.17 | 1 |
| 38 | H3b | C7 | 2.17 | 1 |
| 39 | H7 | C3 | 2.17 | 1 |
| 40 | H5a | C16 | 2.17 | 1 |
| 41 | H5b | C16 | 2.17 | 1 |
| 42 | H16a | C5 | 2.17 | 1 |
| 43 | H16b | C5 | 2.17 | 1 |
| 44 | H5a | C11 | 2.17 | 1 |
| 45 | H5b | C11 | 2.17 | 1 |
| 46 | H11 | C5 | 2.17 | 1 |
| 47 | H13 | C19 | 2.17 | 1 |
| 48 | H19 | C13 | 2.17 | 1 |
| 49 | H7 | C19 | 2.17 | 1 |
| 50 | H19 | C7 | 2.17 | 1 |
| 51 | H7 | C12 | 2.17 | 1 |
| 52 | H12 | C7 | 2.17 | 1 |
| 53 | H9a | C10 | 2.17 | 1 |
| 54 | H9b | C10 | 2.17 | 1 |
| 55 | H10a | C9 | 2.17 | 1 |
| 56 | H10b | C9 | 2.17 | 1 |
| 57 | H11 | C18 | 2.17 | 1 |
| 58 | H18 | C11 | 2.17 | 1 |
| 59 | H12 | C18 | 2.17 | 1 |
| 60 | H18 | C12 | 2.17 | 1 |
| 61 | C1 | C7 | 2.54 | 1 |
| 62 | C11 | C16 | 2.54 | 1 |
| 63 | C5 | C18 | 2.54 | 1 |
| 64 | C7 | C13 | 2.54 | 1 |
| 65 | C7 | C18 | 2.54 | 1 |
| 66 | C11 | C12 | 2.54 | 1 |
| 67 | C3 | C19 | 2.54 | 1 |
| 68 | C12 | C19 | 2.54 | 1 |
| 69 | C3 | C12 | 2.54 | 1 |
| 70 | H1a | H1b | 1.76 | 1 |
| 71 | H1a | H1c | 1.76 | 1 |
| 72 | H1b | H1c | 1.76 | 1 |
| 73 | H3a | H3b | 1.76 | 1 |
| 74 | H5a | H5b | 1.76 | 1 |
| 75 | H8a | H8b | 1.76 | 1 |
| 76 | H9a | H9b | 1.76 | 1 |
| 77 | H10a | H10b | 1.76 | 1 |
| 78 | H16a | H16b | 1.76 | 1 |
| 79 | C8 | C13 | 1.54 | 1 |
| 80 | H8a | C13 | 2.17 | 1 |
| 81 | H8b | C13 | 2.17 | 1 |
| 82 | H13 | C8 | 2.17 | 1 |
| 83 | CO3 | C9 | 1.54 | 1 |
| 84 | CO3 | C10 | 2.54 | 1 |

TABLE 2-continued

Full 145 distance matrix employed for stemona alkaloid synthetic intermediate (atom labelling in this case is arbitrary)

| | Atom 1 | Atom 2 | Distance (Å) | Distance Type[a] |
|---|---|---|---|---|
| 85 | CO3 | C12 | 1.54 | 1 |
| 86 | CO3 | C7 | 2.54 | 1 |
| 87 | CO1 | C9 | 2.54 | 1 |
| 88 | CO1 | C10 | 1.54 | 1 |
| 89 | CO1 | C18 | 2.8 | 2 |
| 90 | CO2 | C13 | 2.54 | 1 |
| 91 | CO2 | C8 | 1.54 | 1 |
| 92 | C5 | C13 | 2.54 | 1 |
| 93 | C8 | C19 | 2.54 | 1 |
| 94 | C11 | C19 | 2.54 | 1 |
| 95 | O3 | CO3 | 1.44 | 1 |
| 96 | O3 | C9 | 2.45 | 1 |
| 97 | O3 | C12 | 2.45 | 1 |
| 98 | O1 | CO1 | 1.4 | 1 |
| 99 | O1 | C10 | 2.45 | 1 |
| 100 | O2 | CO2 | 1.5 | 1 |
| 101 | C16 | C18 | 2.8 | 2 |
| 102 | O11 | CO1 | 1.5 | 1 |
| 103 | O11 | C18 | 1.5 | 1 |
| 104 | O21 | CO2 | 1.5 | 1 |
| 105 | O21 | O2 | 2.45 | 1 |
| 106 | O21 | C19 | 1.5 | 1 |
| 107 | C11 | C13 | 1.5 | 1 |
| 108 | H13 | C11 | 2.17 | 1 |
| 109 | H11 | C13 | 2.17 | 1 |
| 110 | O11 | C16 | 1.5 | 1 |
| 111 | C13 | C18 | 2.54 | 1 |
| 112 | H3b | H19 | 2.91 | 3 |
| 113 | H3b | H12 | 2.79 | 3 |
| 114 | H3b | H10a | 2.94 | 3 |
| 115 | H3b | H7 | 2.32 | 3 |
| 116 | H3b | H1a | 2.27 | 3 |
| 117 | H1a | H19 | 2.26 | 3 |
| 118 | H1a | H12 | 2.62 | 3 |
| 119 | H1a | H7 | 2.41 | 3 |
| 120 | H1a | H3a | 2.46 | 3 |
| 121 | H7 | H19 | 2.65 | 3 |
| 122 | H7 | H18 | 3.56 | 3 |
| 123 | H7 | H16b | 3.21 | 3 |
| 124 | H7 | H8a | 3.06 | 3 |
| 125 | H7 | H5a | 1.99 | 3 |
| 126 | H7 | H3a | 2.56 | 3 |
| 127 | H16a | H18 | 3.27 | 3 |
| 128 | H16a | H11 | 2.63 | 3 |
| 129 | H16a | H5b | 2.23 | 3 |
| 130 | H16a | H5a | 3.32 | 3 |
| 131 | H8a | H16b | 2.87 | 3 |
| 132 | H8a | H11 | 2.2 | 3 |
| 133 | H8a | H5b | 2.26 | 3 |
| 134 | H8a | H5a | 2.9 | 3 |
| 135 | H5b | H18 | 3.51 | 3 |
| 136 | H5a | H19 | 3.6 | 3 |
| 137 | H5a | H18 | 3.72 | 3 |
| 138 | H19 | H8b | 2.66 | 3 |
| 139 | H19 | H13 | 2.08 | 3 |
| 140 | H19 | H12 | 2.28 | 3 |
| 141 | H19 | H3a | 2.26 | 3 |
| 142 | H18 | H12 | 1.9 | 3 |
| 143 | H18 | H9a | 3.4 | 3 |
| 144 | H16b | H5b | 2.74 | 3 |
| 145 | H16b | H5a | 2.18 | 3 |

[a]Type 1 = rigid bonded distance (HSQC, H2BC or aromatic constraint), Type 2 = HMBC distance range ('Distance' entry refers to upper bound), Type 3 = NOE distance.

Result

Figure 4:
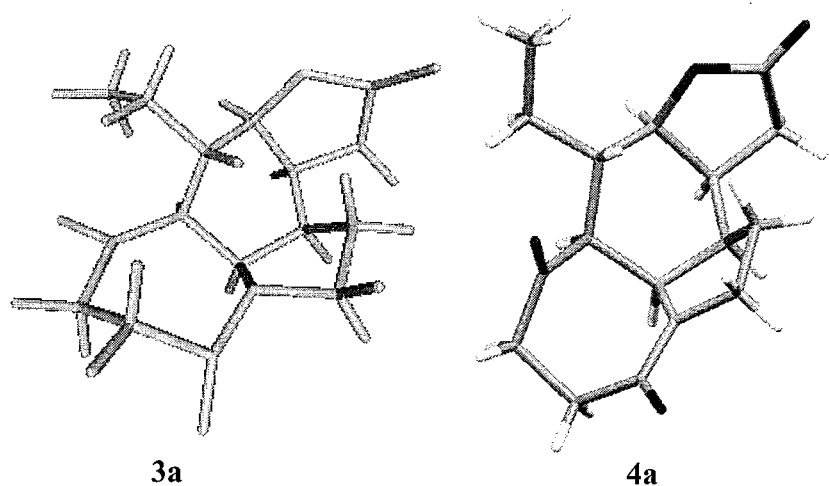
FIG. 4 illustrates the molecular structure of a stemona alkaloid synthetic intermediate geometry determined by the Distance-Geometry method described herein (3a) and by X-ray crystallography (4a).

The solution-state structure (3a in FIG. 4) elucidated is comparable in constitution, configuration and conformation to solid-state structures obtained from X-ray crystallography (4a in FIG. 4). There are some (very small) deviations in the local geometry of the atoms, but these do not detract from the qualitatively correct solution obtained.

The invention claimed is:

1. A method for the determination of the molecular structure of a compound, the method comprising:
a) obtaining one or more nuclear magnetic resonance spectroscopic measurements from the compound, wherein the one or more nuclear magnetic resonance spectroscopic measurements are selected from: X spectra, multidimensional X—X correlation experiments, multidimensional X—Y correlation experiments, nuclear Overhauser effect measurements, rotational Overhauser effect measurements, and a combination thereof; wherein X and Y refer to an active NMR nucleus, and wherein at least one of: the X—X correlation experiments and the X—Y correlation experiments, are selected from: 1-bond correlation experiments, 2-bond correlation experiments, multiple bond correlation experiments, and a combination thereof;
b) determining internuclear distances from the nuclear magnetic resonance spectroscopic measurements; and
c) inputting internuclear distances to a distance-geometry algorithm to determine the probable structure(s) of the compound, wherein the compound has a molecular weight of less than 2000 Daltons and is not a protein.

2. A method as claimed in claim 1, wherein X and Y are independently selected from $^1$H, $^{13}$C, $^{15}$N, $^{19}$F, $^{31}$P, $^{11}$B, $^{29}$Si, $^{17}$O or other NMR active nuclei.

3. A method as claimed in claim 1, wherein the X spectra are 1 dimensional $^1$H spectra, $^{13}$C spectra and/or $^{15}$N spectra.

4. A method as claimed in claim 1, wherein the X—X and/or X—Y correlation experiments are selected from one or more of Heteronuclear Single Quantum Coherence (HSQC), HSQC—Total Correlation Spectroscopy (HSQC-TOCSY), Heteronuclear Multiple Bond Correlation (HMBC), Heteronuclear 2 Bond Correlation (H2BC), Incredible Natural Abundance Double Quantum Transfer Experiment (INADEQUATE), Correlated Spectroscopy (COSY) and Total Correlation Spectroscopy (TOCSY) experiments.

5. A method as claimed in claim 1, wherein the nuclear Overhauser effect or rotational Overhauser effect measurements are selected from one or more of NOE or ROE, and X—X NOE or ROE measurements, wherein X is preferably $^1$H.

6. A method as claimed in claim 1, further comprising a step of estimating internuclear distances by assuming average, standard bond distances based on connectivity from 1-bond X—X or X—Y correlation experiments and inputting the estimated distances to the distance-geometry algorithm.

7. A method as claimed in claim 1, further comprising a step of estimating typical bond or through-space distances based on connectivity from 2-bond correlation experiments and inputting the estimated distances to the distance-geometry algorithm.

8. A method as claimed in claim 1, further comprising a step of determining estimated ranges of values of distances based on multiple bond correlation experiments and inputting the estimated maximum values to the distance-geometry algorithm.

9. A method as claimed in claim 1, wherein determining the internuclear distances is from the NOE and/or ROE measurements.

10. A method as claimed in claim 1, further comprising the step, before obtaining the NMR spectroscopic measurements, of providing a compound and dissolving the compound in an NMR acceptable solvent to obtain a solution.

11. A method as claimed in claim 10, wherein the NMR acceptable solvent is a deuterated solvent.

12. A method as claimed in claim 1, wherein the compound contains C and H atoms.

13. A method as claimed in claim 1, wherein the distance-geometry algorithm is computer implemented.

14. A method as claimed in claim 1, wherein the method does not comprise a step of comparing the NMR spectroscopic measurements to a computer database of known NMR spectroscopic measurements, nor known molecular structures, during the generation of possible structural candidates.

15. A method as claimed in claim 1, which comprises an additional step (d) inputting a constraint to the algorithm and repeating step (c).

16. A method as claimed in claim 15, wherein inputting a constraint comprises at least one of: (i) modifying distance constraints for H—C and C—C distances to account for the hybridisation at carbon centers;
- (ii) constraining known chemical features to physically reasonable geometries;
- (iii) introducing at least one of: distances of other nuclei, and connectivity of other nuclei;
- (iv) modifying Type 2 distance ranges to recognize the bonding which is apparent in the structure solution; and
- (v) adding distances based on additional spectroscopic information available.

17. A method as claimed in claim 1, wherein the X—X and/or X—Y correlation experiments are selected from one or more of: Heteronuclear Multiple Bond Correlation (HMBC), Heteronuclear 2 Bond Correlation (H2BC), Incredible Natural Abundance Double Quantum Transfer Experiment (INADEQUATE), and Correlated Spectroscopy (COSY) experiments.

18. A method as claimed in claim 1, wherein the distance-geometry algorithm comprises global optimization of a figure of merit function relating structure to the goodness of fit between distances in the structure and an input distance matrix.

19. A method as claimed in claim 18, wherein the merit function comprises a sum of distance constraint terms.

* * * * *